United States Patent
Suzuki et al.

(10) Patent No.: US 10,314,464 B2
(45) Date of Patent: Jun. 11, 2019

(54) INSERTION APPARATUS

(71) Applicant: OLYMPUS CORPORATION, Tokyo (JP)

(72) Inventors: Takashi Suzuki, Hino (JP); Takashi Yamashita, Hachioji (JP); Yoshitaka Umemoto, Hachioji (JP); Fumiyuki Onoda, Tama (JP); Takuro Onda, Sagamihara (JP); Yasuaki Hirata, Akishima (JP); Takahiro Shibata, Fuchu (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/613,924

(22) Filed: Jun. 5, 2017

(65) Prior Publication Data
US 2017/0265717 A1    Sep. 21, 2017

Related U.S. Application Data

(63) Continuation of application No. PCT/JP2015/083765, filed on Dec. 1, 2015.

(30) Foreign Application Priority Data

Dec. 25, 2014    (JP) ................. 2014-263392

(51) Int. Cl.
*A61B 1/31*    (2006.01)
*A61B 1/00*    (2006.01)
(Continued)

(52) U.S. Cl.
CPC ........ *A61B 1/0016* (2013.01); *A61B 1/00006* (2013.01); *A61B 1/0051* (2013.01);
(Continued)

(58) Field of Classification Search
CPC ........... A61M 25/0105; A61M 25/0116; A61B 1/00131; A61B 1/00133; A61B 1/00156;
(Continued)

(56) References Cited

U.S. PATENT DOCUMENTS

| | | | |
|---|---|---|---|
| 2008/0262305 A1* | 10/2008 | Omoto | A61B 1/00154 600/118 |
| 2009/0156897 A1 | 6/2009 | Omot et al. | |
| 2012/0302831 A1 | 11/2012 | Ashida et al. | |
| 2014/0316201 A1 | 10/2014 | Umemoto | |

FOREIGN PATENT DOCUMENTS

| | | |
|---|---|---|
| CN | 1933763 A | 3/2007 |
| CN | 104080391 A | 10/2014 |

(Continued)

OTHER PUBLICATIONS

Chinese Office Action dated Aug. 23, 2017 in Chinese Patent Application No. 201580033831.1.
(Continued)

*Primary Examiner* — Ryan N Henderson
*Assistant Examiner* — Pamela F WU
(74) *Attorney, Agent, or Firm* — Scully, Scott, Murphy & Presser, P.C.

(57) ABSTRACT

An insertion apparatus includes an insertion section, a rotational housing, a motor, and a controller. The motor rotates the rotational housing. The controller designates a rotational direction of the motor. The controller limits the rotational direction of the motor to allow the insertion section to move only in a removal direction when inspection control for inspecting an operation relative to an insertion direction of the insertion section is initiated.

7 Claims, 7 Drawing Sheets

(51) Int. Cl.
  *G02B 23/24* (2006.01)
  *A61B 1/005* (2006.01)
  *A61B 34/30* (2016.01)
(52) U.S. Cl.
  CPC ...... *A61B 1/00057* (2013.01); *A61B 1/00135* (2013.01); *A61B 1/31* (2013.01); *G02B 23/24* (2013.01); *G02B 23/2407* (2013.01); *G02B 23/2461* (2013.01); *G02B 23/2476* (2013.01); *G02B 23/2484* (2013.01); *A61B 1/00002* (2013.01); *A61B 1/00043* (2013.01); *A61B 1/00045* (2013.01); *A61B 1/00147* (2013.01); *A61B 2034/301* (2016.02)
(58) Field of Classification Search
  CPC ..... A61B 1/0016; A61B 1/005; A61B 1/0051; A61B 1/01; A61B 1/31; A61B 2034/301; G02B 23/24; G02B 23/2407; G02B 23/2461; G02B 23/2484
  USPC .......................................................... 600/114
  See application file for complete search history.

(56) References Cited

FOREIGN PATENT DOCUMENTS

| | | |
|---|---|---|
| JP | H07-116112 A | 5/1995 |
| JP | 2007-307241 A | 11/2007 |
| JP | 5025319 B2 | 9/2012 |
| JP | 2012-245052 A | 12/2012 |
| JP | 2014-004268 A | 1/2014 |
| JP | 2014-064686 A | 4/2014 |

OTHER PUBLICATIONS

English translation of International Preliminary Report on Patentability dated Jul. 6, 2017 together with the Written Opinion received in related International Application No. PCT/JP2015/083765.
International Search Report dated Mar. 1, 2016 issued in PCT/JP2015/083765.
Extended Supplementary European Search Report dated Jul. 3, 2018 in European Patent Application No. 15 87 2642.2.

* cited by examiner

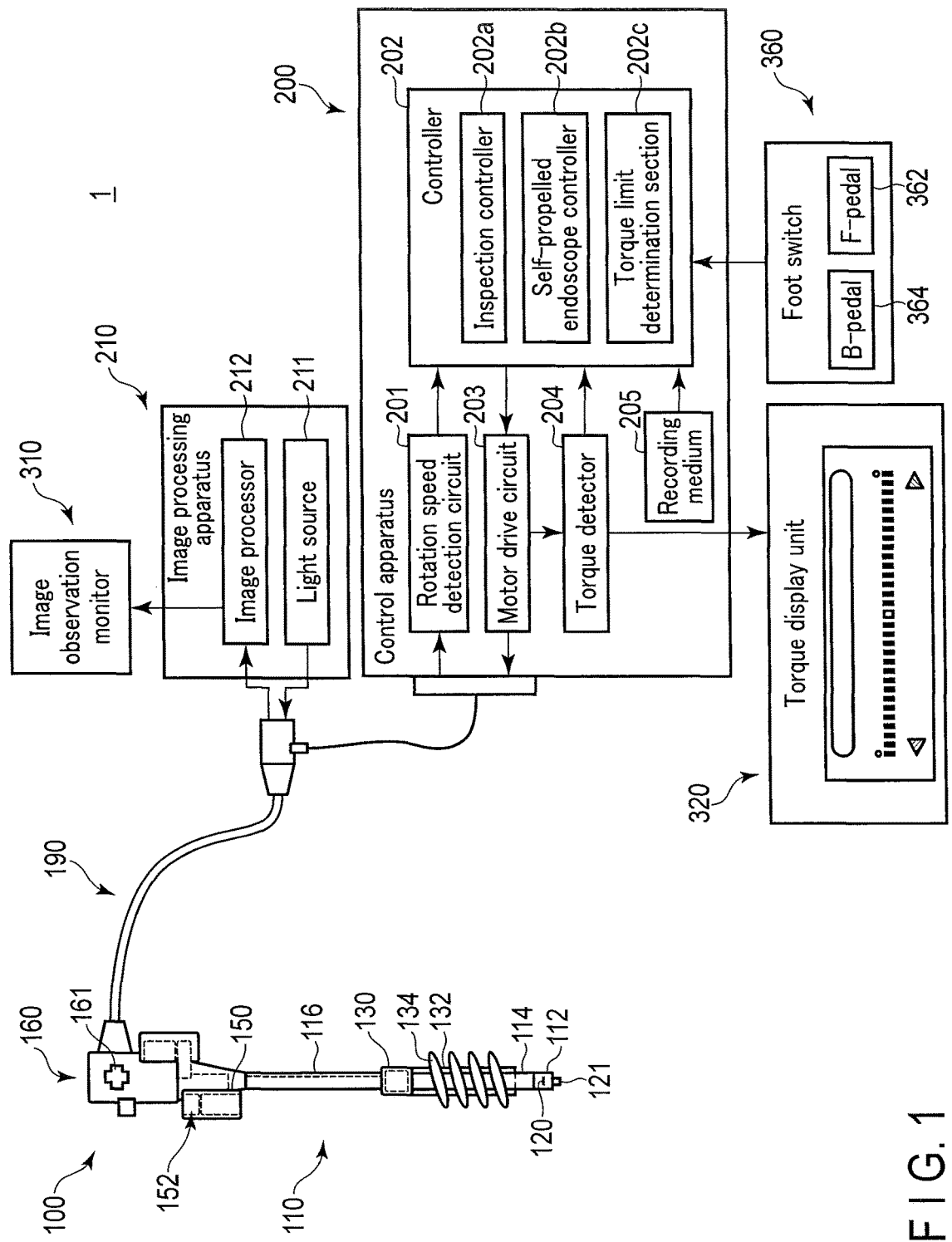
F I G. 1

INSERTION APPARATUS

CROSS-REFERENCE TO RELATED APPLICATIONS

This application is a Continuation Application of PCT Application No. PCT/JP2015/083765, filed Dec. 1, 2015 and based upon and claiming the benefit of priority from the prior Japanese Patent Application No. 2014-263392, filed Dec. 25, 2014, the entire contents of both of which are incorporated herein by reference.

BACKGROUND OF THE INVENTION

1. Field of the Invention

The present invention relates to a rotary self-propelled type insertion apparatus.

2. Description of the Related Art

Generally, an insertion apparatus such as an endoscope apparatus is inserted into a lumen. Among these types of insertion apparatuses, an insertion apparatus which is called a rotary self-propelled type has been known.

For example, the endoscope apparatus described in Jpn. Pat. Appln. KOKAI Publication No. 2007-307241 is a rotary self-propelled type endoscope apparatus. The rotary self-propelled type endoscope apparatus as described in Jpn. Pat. Appln. KOKAI Publication No. 2007-307241, for example, is provided with a rotating cylinder, which is called a power spiral tube, in which a spiral-shaped fin is formed on an outer peripheral surface of the insertion section. When the rotating cylinder is rotated, the fin formed to the rotating cylinder is brought into contact with an inner wall of a lumen, and generates stress. The insertion section self-propels in an insertion direction or in a removal direction by the stress.

The in vivo insertion apparatus, which is a rotary self-propelled type endoscope described in Jpn. Pat. Appln. KOKAI Publication No. 2014-64686, inspects the state of the apparatus before starting observation. The in vivo insertion apparatus detects whether a lubricant is suitably applied to a spiral tube before starting observation. That is, the in vivo insertion apparatus actually rotates the spiral tube and determines whether a lubricant is suitably applied based on the amount of driving current of a motor. The in vivo insertion apparatus then proceeds with an observation process only for the normal state, namely, when it is determined that the lubricant is suitably applied to the spiral tube.

BRIEF SUMMARY OF THE INVENTION

An insertion apparatus according to an aspect of the invention comprises: an insertion section having an elongated shape; a rotational housing provided on an outer peripheral surface of the insertion section to be rotatable about a longitudinal axis; a motor that rotates the rotational housing; a fin formed on an outer peripheral surface of the rotational housing as a spiral shape, and arranged to allow the insertion section to move in an insertion direction in which the insertion section is to be inserted into an internal body, or in a removal direction in which the insertion section is to be removed from the internal body, along with rotation of the rotational housing; and a controller that designates a rotational direction and a rotational speed of the motor, wherein the controller limits the rotational direction of the motor to allow the insertion section to move only in the removal direction when inspection control for inspecting an operation relative to the insertion direction of the insertion section is initiated.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute apart of the specification, illustrate embodiments of the invention, and together with the general description given above and the detailed description of the embodiments given below, serve to explain the principles of the invention.

FIG. 1 is a schematic view of an example configuration of an insertion apparatus according to an embodiment of the present invention;

DETAILED DESCRIPTION OF THE INVENTION

Figure 2:
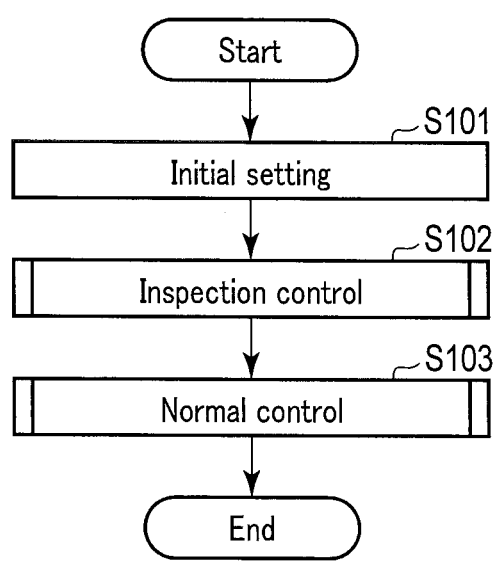
FIG. 2 is a flowchart showing an example operation of the insertion apparatus according to an embodiment of the present invention.

FIG. 1 is a schematic view of a configuration of an endoscope system as an example of an insertion apparatus according to an embodiment of the present invention. As shown in FIG. 1, the insertion apparatus 1 includes an endoscope 100, a control apparatus 200, an image processing apparatus 210, an image observation monitor 310, a torque display unit 320, and a foot switch 360. The endoscope 100 is a rotary self-propelled type endoscope, and is provided with an insertion section 110. The insertion section 110 is an elongated shape, and is configured to be internally inserted into a body. The endoscope 100 also is provided with a control unit 160 by which various operations for the endoscope 100 are performed. The control unit 160 is held by a user. In the following explanation, the side of a distal end of the insertion section 110 is referred to as a distal end side. The side of the insertion section 110 in which the control unit 160 is provided is referred to as a proximal end side. The direction from the distal end and the proximal end of the insertion section 110 is referred to as a longitudinal direction. The control unit 160, the control apparatus 200, and the image processing apparatus 210 of the endoscope 100 are connected by a universal cable 190.

The insertion section 110 includes a distal end hard section 112, a bending section 114, and a coiled hose section 116. The distal end hard section 112 is an edge of the distal end of the insertion section 110, and is formed to not be bent. The bending section 114 is a section formed at the proximal end side of the distal end hard section 112, and is formed to be actively bent in accordance with an operation of an operating section 161 provided to the control unit 160. The coiled hose section 116 is a section formed at the proximal end side of the bending section 114, and is formed to be passively bent by external force.

The distal end hard section 112 includes an image sensor 120 and an illumination lens 121. The image sensor 120 generates an image signal based on a subject image at the distal end side of the insertion section 110, for example. The image signal generated by the image sensor 120 is transmitted to an image processing apparatus 210 via a signal line for an image signal (not shown in the drawings) passing through the insertion section 110 and the universal cable 190. The illumination lens 121 diffuses and emits light guided from the image processing apparatus 210 through an optical fiber (not shown in the drawings) passing through the insertion section 110 and the universal cable 190.

The coiled hose section 116 of the insertion section 110 is provided with a rotating section 130 that transfers driving power of a motor 150 installed in the control unit 160. The rotating section 130 is provided with a power spiral tube 132 which is a rotational housing at the distal end. The power spiral tube 132 is formed of a soft material such as a rubber or a resin, for example, in a cylindrical shape, and is mounted rotatably around the longitudinal axis of the coiled hose section 116. The power spiral tube 132 is provided with a spiral fin 134 along the longitudinal axis of the power spiral tube 132 on the outer peripheral surface. The power spiral tube 132 may be configured to be removable from the rotating section 130.

The power spiral tube 132 is connected to the motor 150 provided to the control unit 160 as an actuator. The motor 150 is connected to the control apparatus 200 via a signal line for an actuator current signal (not shown in the drawings) passing through the control unit 160 and the universal cable 190.

The motor 150 operates by an operation using the foot switch 360. The rotative power of the motor 150 is transferred to the rotating section 130. As a result, the fin 134 provided to the power spiral tube 132 is rotated around the longitudinal axis.

When the fin 134 rotates in the state of being in contact with a wall part such as an inner wall of a lumen, stress is generated to allow the insertion section 110 to self-propel. For example, in a small intestine or a large intestine, the fin 134 draws folds in the inner wall of the small intestine or the large intestine so that stress is applied to the insertion section 110. The insertion section 110 self-propels by the stress. The self-propelling of the insertion section 110 assists the insertion operation or the removal operation of the insertion section 110 by the user. In the following explanation, the direction of rotation of the motor 150 to allow the insertion section 110 to self-propel toward the distal end side is referred to as a normal rotation direction (insertion direction), and the direction of rotation of the motor 150 to allow the insertion section 110 to self-propel toward the proximal end side is referred to as a reverse rotation direction (removal direction).

The motor 150 is provided with a pulse generator 152. The pulse generator 152 generates a pulse signal (rotational speed signal) in accordance with the rotational speed of the motor 150, and inputs the rotational speed signal to the control apparatus 200 via a signal line for rotational speed (not shown in the drawings) passing through the universal cable 190.

The image observation monitor 310 includes a general display element such as a liquid crystal display, for example. The image observation monitor 310 displays an endoscope image based on an image signal obtained by the image sensor 120, for example.

The foot switch 360 includes a forward pedal (F-pedal) 362, and a backward pedal (B-pedal) 364. The F-pedal 362 generates an instruction signal to allow the motor 150 to perform normal rotation by the user stepping on the pedal. The B-pedal 364 generates an instruction signal to allow the motor 150 to perform reverse rotation by the user stepping on the pedal. The F-pedal 362 and the B-pedal 364 each are configured to generate a signal having a magnitude in accordance with the amount of the stepping. The motor 150 performs normal rotation with a rotational speed in accordance with the amount of stepping on the F-pedal 362. The motor 150 performs reverse rotation with a rotational speed in accordance with the amount of stepping on the B-pedal 364.

The torque display unit 320 is a display device formed by using a display element such as an LED, for example, and performs display based on a display signal input from a torque detector 204.

The control apparatus 200 controls each element of the insertion apparatus 1. The control apparatus 200 is provided with a rotation speed detection circuit 201, a controller 202, a motor drive circuit 203, and a torque detector 204.

The rotation speed detection circuit 201 obtains a rotational speed signal input from the pulse generator 152 for each predetermined sampling period, and inputs the obtained rotational speed signal to the controller 202. The controller 202 supplies to the motor drive circuit 203 a motor current allowing a rotational speed to be a speed in accordance with the amount of stepping on the F-pedal 362 and the B-pedal 364 by using the rotational speed signal as a feedback signal.

The motor drive circuit 203 drives the motor 150 based on a command value in accordance with a difference between the present motor speed calculated at the controller 202 and a target motor speed. The motor drive circuit 203 is formed of a driver amplification circuit, for example.

The torque detector 204 acting as a motor current detector normalizes a current value of the motor current output from the motor drive circuit 203, and outputs a signal of the normalized current value as a display signal. It is also possible that the amount of torque calculated based on the motor current is normalized. In addition, the torque detector 204 also outputs the motor current to the controller 202.

A recording medium 205 is a recording medium in which data is stored even if a power is turned off, such as a flash memory, and records data such as a program or a torque limit setting value, etc. to operate the control apparatus 200.

The controller 202 includes an inspection controller 202*a*, a self-propelled endoscope controller 202*b*, and a torque limit determining section 202*c*.

The inspection controller 202*a* performs inspection control. The inspection control is to allow a user to perform operation inspection of the endoscope 100. The self-propelled endoscope controller 202*b* performs normal control. The normal control is control for observation.

The torque limit determining section 202*c* determines whether or not to apply a torque limit to the motor 150 by determining whether the amount of the motor current output by the torque detector 204 exceeds a torque limit setting value which is a predetermined current threshold. The torque limit determining section 202*c* determines to apply the torque limit to the motor 150 when it is determined that the motor current exceeds the torque limit setting value. The torque limit is to suppress the torque of the motor 150 by stopping supply of a motor current to the motor drive circuit 203 by the controller 202. The motor 150 stops rotation in the removal direction when the torque limit is applied when rotating in the removal direction. The motor 150 stops rotation in the insertion direction when the torque limit is applied when rotating in the insertion direction.

The image processing apparatus 210 is provided with a light source 211 and an image processor 212. The light source 211 is, for example, a white LED or a xenon lamp, and inputs light to the optical fiber not shown in the drawings within the universal cable 190. The light is emitted from the illumination lens 121.

The image processor 212 performs image processing to an image signal input to the image processor 212 through the insertion section 110 and the universal cable 190. The image processor 212 inputs the processed image signal to the image observation monitor 310 to display an endoscope image on the image observation monitor 310.

The operation of the insertion apparatus 1 according to an embodiment of the present invention will be explained. FIG. 2 is a flowchart showing an example operation of the insertion apparatus 1. The operation shown in FIG. 2 is controlled by the controller 200. The operation starts when the insertion apparatus 1 is powered on, for example. Along with the operation shown in FIG. 2, processing such as displaying an endoscope image based on the image signal obtained at the image sensor 120 on the image observation monitor 310 is performed.

In step S101, the controller 202 performs initial setting. In the initial setting, the connection between the endoscope 100 and the control apparatus 200 is checked, for example. Then, the processing proceeds to step S102.

Figure 3:
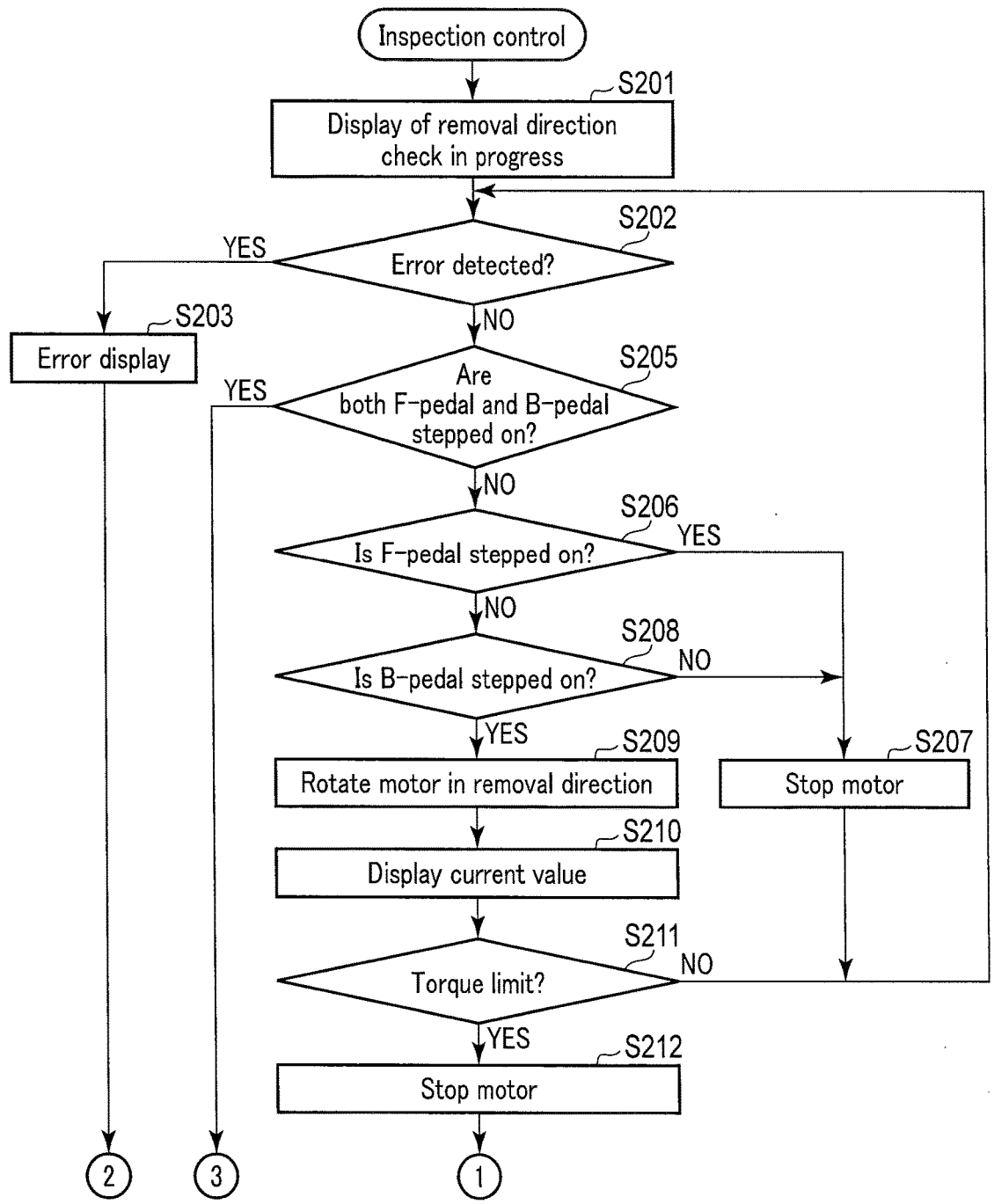
FIG. 3 is a flowchart showing an example operation of inspection control.
Figure 4:
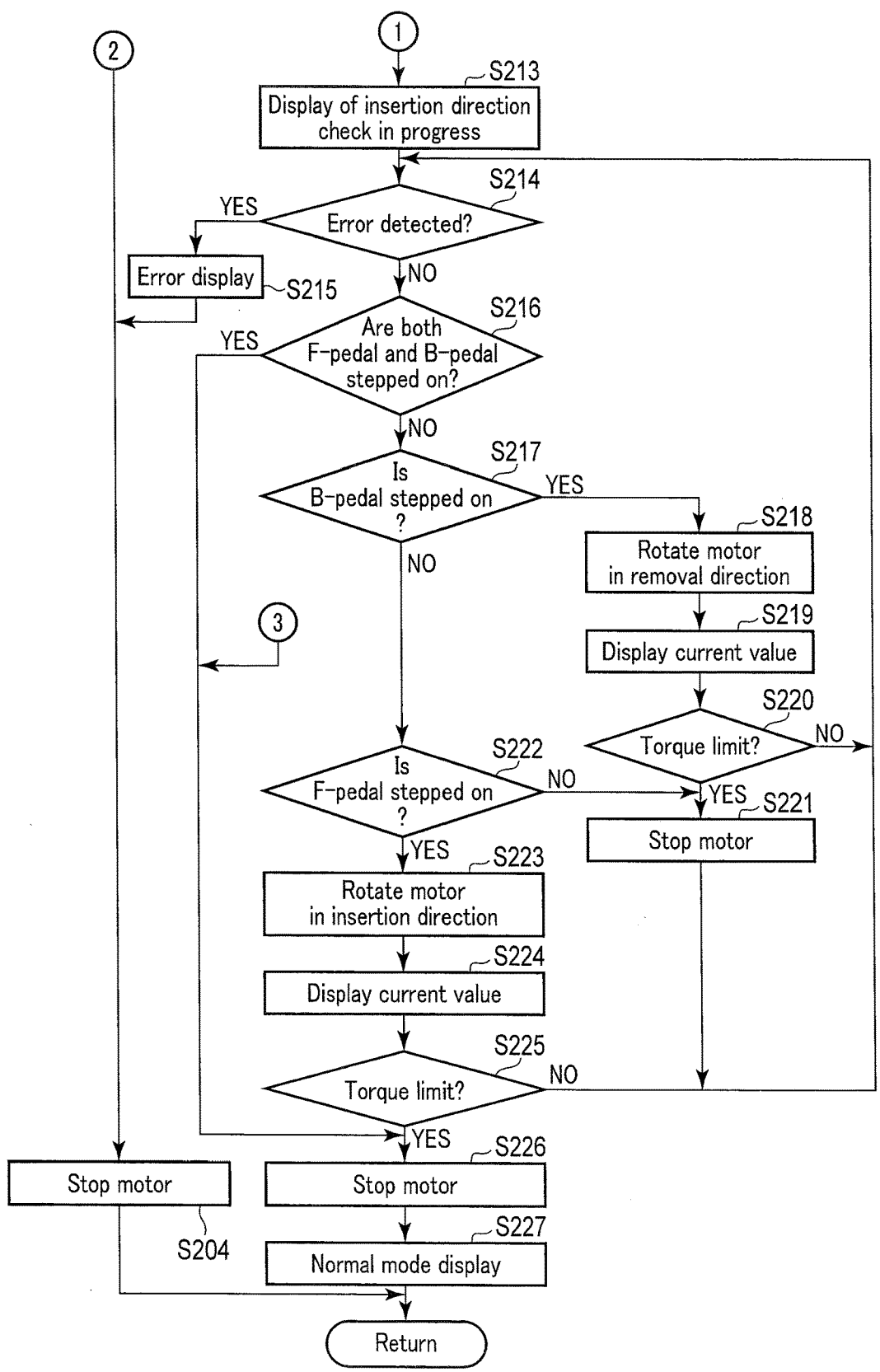
FIG. 4 is a flowchart showing an example operation of inspection control.

In step S102, the controller 202 performs inspection control. The inspection control will be explained below. FIGS. 3 and 4 are a flowchart illustrating the inspection control. In the inspection control, a removal direction check for checking the operation of the insertion section 110 in the removal direction is first performed, and then an insertion direction check for checking the operation of the insertion section 110 in the insertion direction is performed.

In step S201, the controller 202 allows the torque display unit 320 to indicate that the removal direction check is in progress.

Figure 5:
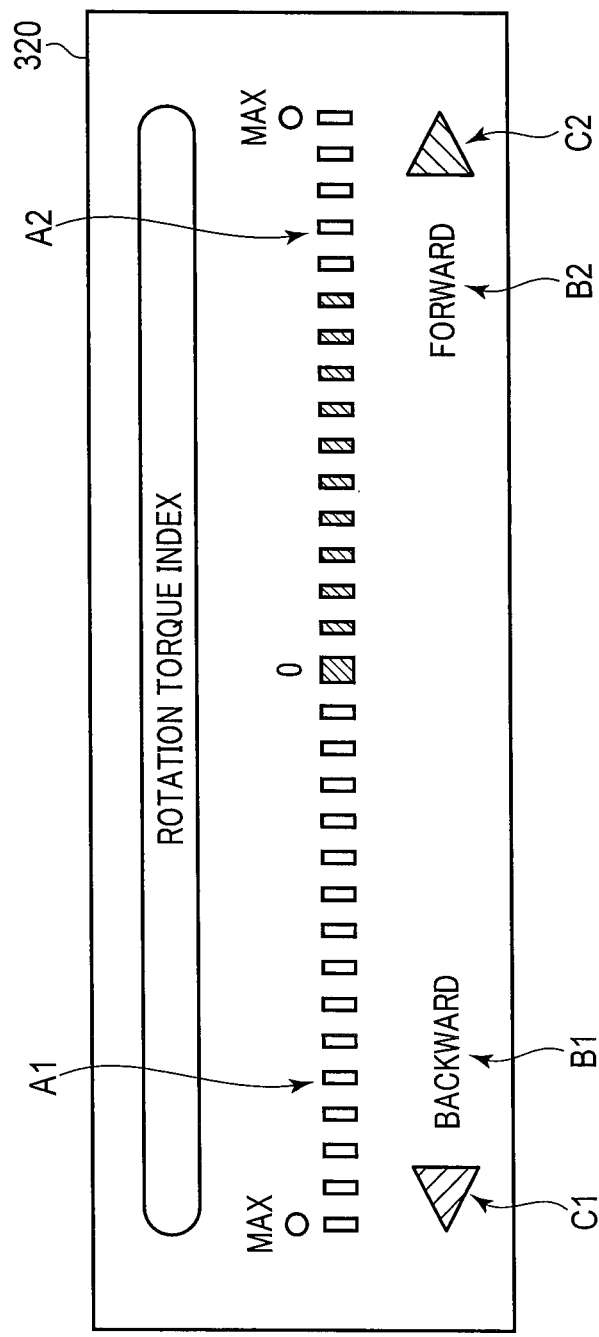
FIG. 5 explains a display of a torque display unit.

The display by the torque display unit 320 will be explained with reference to FIG. 5. FIG. 5 is an example of a torque display of the motor 150 by a level meter. The display surface of the torque display unit 320 includes a removal direction level display part A1, an insertion direction level display part A2, a removal direction text (BACKWARD) display part B1, an insertion direction text (FORWARD) display part B2, an arrow display part C1, and an arrow display part C2. Each display part is formed, for example, by LEDs.

The removal direction level display part A1 is provided at the left side from the level of "0". The removal direction level display part A1 has a level display part having 15 levels which are sequentially turned on in accordance with the amount of the motor's current to allow the motor 150 to perform reverse rotation. On the other hand, the insertion direction level display part A2 is provided at the right side from the level of "0". The insertion direction level display part A2 has a level display part having 15 levels which are sequentially turned on in accordance with the amount of the motor current to allow the motor 150 to perform normal rotation. The level of "0" is always turned on, for example. For example, when the motor 150 performs normal rotation, the insertion direction level display part A2 is turned on in accordance with the amount of the motor current, as shown in FIG. 5.

The removal direction text display part B1 is provided to display a text "BACKWARD", and is turned on, turned off, or blinks. That is, the removal direction text display part B1 is turned on for the normal control, blinks when indicating that a removal direction check is in progress, and is turned off when indicating that an insertion direction check is in progress that will be explained later. The insertion direction text display part B2 is provided to display a text "FORWARD", and is turned on, turned off, or blinks. That is, insertion direction text display part B2 is turned on for the normal control, is turned off when indicating that the removal direction check is in progress, and blinks when indicating that the insertion direction check is in progress as will be explained later.

The arrow display part C1 is turned on, turned off, or blinks in the manner similar to the removal direction text display part B1. That is, the arrow display part C1 is turned on for the normal control, blinks when indicating that the removal direction check is in progress, and is turned off when indicating that the insertion direction check is in progress as will be explained later. The arrow display part C2 is turned on, turned off, or blinks in the manner similar to the insertion direction text display part B2. That is, the arrow display part C2 is turned on for the normal control, is turned off when indicating that the removal direction check is in progress, and blinks when indicating that the insertion direction check is in progress that will be explained later.

Next, the display of indicating that the removal direction check is in progress will be explained. As stated above, when indicating that the removal direction check is in progress, the removal direction text display part B1 and the arrow display part C1 both blink, and the insertion direction text display part B2 and the arrow display part C2 both are turned off. That is, when indicating that the removal direction check is in progress, only the display parts in the removal direction blink, and the user can recognize that an inspection in the removal direction should be performed.

The explanation returns to FIG. 3. The inspection by the user explained below is performed by the user holding the insertion section 110 by one hand to prevent the insertion section 110 from rotating, for example. In the state where the insertion section 110 is held to prevent the rotation, when the controller 202 supplies the motor current to the motor 150, torque is generated in the motor 150. In this case, the torque is applied to a user's fingers. As the amount of stepping on the foot switch 360 increases, the torque generated in the motor 150 becomes larger. When the value of the motor current is equal to or greater than the torque limit setting value, the torque limit is applied, and the rotation of the motor 150 is stopped. By this operation, the user can recognize that the motor 150 rotates in accordance with the amount of stepping on the foot switch 360, and that the torque limit is normally applied.

In step S202, the controller 202 determines whether or not an error is detected. The error includes a situation where the connection state of each member is not confirmed, or where the rotation of the motor 150 is not detected even though a motor current is output, for example. When an error is detected in step S202, the controller 202 performs error display to the torque display unit 320 in step S203. Then, the processing proceeds to step S204. The details of error display will be described later.

In step S204, the controller 202 stops output of the motor current to stop the rotation of the motor 150. After that, the inspection control is terminated.

When an error is not detected in step S202, the controller 202 determines whether or not both of the F-pedal 362 and the B-pedal 364 are stepped on in step S205. When both of the F-pedal 362 and the B-pedal 364 are stepped on, the inspection control is forcibly terminated. When it is determined that both of the F-pedal 362 and the B-pedal 364 are stepped on in step S205, the processing proceeds to step S226. When it is determined that both of the F-pedal 362 and the B-pedal 364 are not stepped on in step S205, the controller 202 determines whether or not the F-pedal 362 is stepped on in step S206.

When it is determined that the F-pedal 362 is stepped on in step S206, the controller 202 stops supplying of the motor current to the motor drive circuit 203 to stop the rotation of the motor 150 in step S207. Then, the processing returns to step S202. That is, during the removal direction check, the insertion section 110 does not move toward the insertion direction.

When it is determined that the F-pedal 362 is not stepped on in step S206, the controller 202 determines whether or not the B-pedal 364 is stepped on in step S208. When it is determined that the B-pedal 364 is not stepped on in step S208, the processing proceeds to step S207.

When it is determined that the B-pedal 364 is stepped on in step S208, the controller 202 supplies the motor current in the removal direction to the motor 150 through the motor drive circuit 203, so that the fin 134 performs reverse rotation with a rotational speed in accordance with the amount of stepping on the B-pedal 364 by the user, in step S209. Then, the processing proceeds to step S210.

In step S210, the torque detector 204 generates a display signal based on the motor current value output from the motor drive circuit 203, and allows the torque display unit 320 to perform display based on the generated display signal. That is, the torque detector 204 allows a larger number of levels of the removal direction level display part A1 to be turned on, as the motor current value increases. Then, the processing proceeds to step S211.

In step S211, the controller 202 determines whether or not to apply the torque limit to the motor 150, by determining whether the motor current value obtained from the torque detector 204 exceeds the torque limit setting value. When it is determined to not apply the torque limit to the motor 150 in step S211, namely, that the motor current value obtained from the torque detector 204 is less than the torque limit setting value, the processing returns to step S202.

When it is determined to apply the torque limit to the motor 150 in step S211, namely, the amount of torque input to the torque limit determining section 202c is equal to or greater than the torque limit setting value, the controller 202 stops supplying the motor current to the motor drive circuit 203 to stop the rotation of the motor 150 in step S212. Then, the processing proceeds to step S213.

In step S213, the controller 202 allows the torque display unit 320 to indicate that the insertion direction check is in progress. The display of indicating that the insertion direction check is in progress is to indicate that the inspection of the torque limit in the insertion direction is initiated.

The display of indicating that the insertion direction check is in progress will be explained. As stated above, when indicating that the insertion direction check is in progress, the removal direction text display part B1 and the arrow display part C1 are both turned off, and the insertion direction text display part B2 and the arrow display part C2 both blink. That is, when indicating that the insertion direction check is in progress, only the display parts in the insertion direction blink, and the user can recognize that inspection in the insertion direction should be performed.

In step S214, the controller 202 determines whether or not an error is detected. When it is determined that an error is detected in step S214, the controller 202 allows the torque display unit 320 to perform error display in step S215. Then, the processing proceeds to step S204. The details of error display will be described later.

When it is determined that an error is not detected in step S214, the controller 202 determines whether or not both of the F-pedal 362 and the B-pedal 364 are stepped on in step S216. When it is determined that both of the F-pedal 362 and the B-pedal 364 are stepped on in step S216, the processing proceeds to step S226, and the rotation of the motor 150 is stopped.

When it is determined that both of the F-pedal 362 and the B-pedal 364 are not stepped on in step S216, the controller 202 determines whether or not the B-pedal 364 is stepped on in step S217. When it is determined that the B-pedal 364 is stepped on in step S217, the controller 202 outputs a motor current to allow the motor 150 to rotate in the removal direction in step S218. The motor 150 performs reverse rotation due to the motor current. The rotation operation in the removal direction is also allowed in the case of performing the insertion direction check for safety.

In step S219, the torque detector 204 generates a display signal based on the motor current value output from the motor drive circuit 203, and allows the torque display unit 320 to perform display based on the generated display signal. That is, the torque detector 204 allows a larger number of levels of the removal direction level display part A1 to be turned on, as the motor current value increases. Then, the processing proceeds to step S220.

In step S220, the controller 202 determines whether or not to apply the torque limit to the motor 150. When it is determined to not apply the torque limit to the motor 150 in step S220, the processing returns to step S214. When it is determined to apply the torque limit to the motor 150 in step S220, the controller 202 stops supplying of the motor current to the motor drive circuit 203 to stop the rotation of the motor 150 in step S221. Then, the processing returns to step S214.

When it is determined that the B-pedal 364 is not stepped on in step S217, the controller 202 determines whether or not the F-pedal 362 is stepped on in step S222. When it is determined that the F-pedal 362 is not stepped on in step S222, the processing proceeds to step S221.

When it is determined that the F-pedal 362 is stepped on in step S222, the controller 202 outputs a motor current to allow the motor 150 to rotate in the insertion direction in step S223. Then, the processing proceeds to step S224.

In step S224, the torque detector 204 generates a display signal based on the motor current value output from the motor drive circuit 203, and allows the torque display unit 320 to perform display based on the generated display signal. That is, the torque detector 204 allows a larger number of levels of the insertion direction level display part A2 to be turned on, as the motor current value increases. Then, the processing returns to step S225.

In step S225, the controller 202 determines whether or not to apply the torque limit to the motor 150. When it is determined not to apply the torque limit to the motor 150 in step S225, the processing returns to step S214. When it is determined to apply the torque limit in step S225, the processing proceeds to step S226.

In step S226, the controller 202 stops supplying the motor current to the motor drive circuit 203 to stop the rotation of the motor 150. Then, in step S227, the controller 202 performs normal mode display on the torque display unit 320. After the inspection control is terminated, the processing returns to the motor control.

In the normal mode display, all of the removal direction text display part B1 and the arrow display part C1, the insertion direction text display part B2, and the arrow display part C2 are turned on. That is, the display is different from the cases of the removal direction check and insertion direction check. Accordingly, the user can recognize that the operation is transferred to the normal control.

Figure 6:
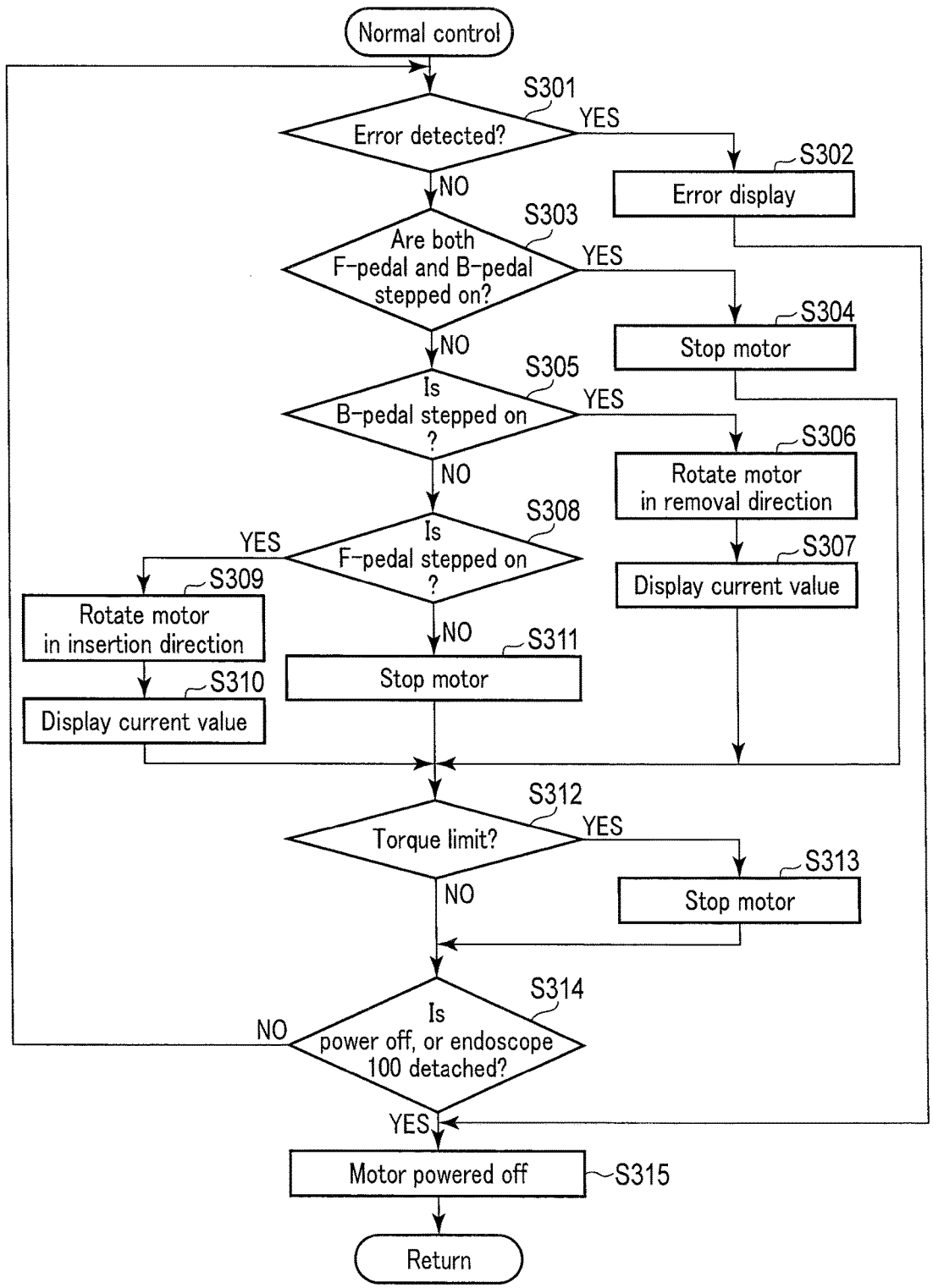
FIG. 6 is a flowchart showing normal control.

The explanation returns to FIG. 2. After the inspection control in step S102, the controller 202 performs normal control in step S103. FIG. 6 is a flowchart illustrating the normal control.

In step S301, the controller 202 determines whether or not an error is detected. When an error is detected in step S301, the controller 202 allows the torque display unit 320 to perform error display in step S302. Then, the processing proceeds to step S315. The details of error display will be described later.

When it is determined that an error is not detected in step S301 the controller 202 determines whether or not both of the F-pedal 362 and the B-pedal 364 are stepped on in step S303. When it is determined that both of the F-pedal 362 and the B-pedal 364 are stepped on in step S303, the controller 202 stops output of the motor current to stop the rotation of the motor 150 in step S304. Then, the processing proceeds to step S312.

When it is determined that both of the F-pedal 362 and the B-pedal 364 are not stepped on in step S303, the controller 202 determines whether or not the B-pedal 362 is stepped on in step S305.

When it is determined that the B-pedal 362 is stepped on in step S305, the controller 202 supplies the motor current in the removal direction to the motor 150 through the motor drive circuit 203 in step S306. After that, the torque detector 204 generates a display signal based on the motor current value output from the motor drive circuit 203, and allows the torque display unit 320 to perform display based on the generated display signal in step S307. Then, the processing proceeds to step S312.

When it is determined that the B-pedal 362 is not stepped on in step S305, the controller 202 determines whether or not the F-pedal 364 is stepped on in step S308. When it is determined that the F-pedal 364 is stepped on in step S308, the controller 202 supplies the motor current in the insertion direction to the motor 150 through the motor drive circuit 203 in step S309. Then, the processing proceeds to step S310.

In step S310, the torque detector 204 generates a display signal based on the motor current value output from the motor drive circuit 203, and allows the torque display unit 320 to perform display based on the generated display signal. Then, the processing proceeds to step S312.

When it is determined that the F-pedal 364 is not stepped on in step S308, the controller 202 stops supplying of the motor current to stop the rotation of the motor 150 in step S311. Then, the processing proceeds to step S312.

In step S312, the controller 202 determines whether or not to apply the torque limit. When it is determined not to apply the torque limit in step S312, the processing proceeds to step S314. When it is determined to apply the torque limit in step S312, the controller 202 stops supplying of the motor current to stop the rotation of the motor 150 in step S313. Then, the processing proceeds to step S314.

In step S314, the controller 202 determines whether or not the endoscope system 1 is powered off, or whether or not the endoscope 100 of the insertion apparatus 1 is detached from the control apparatus 200. When it is determined that the endoscope system 1 is not powered off, and the endoscope 100 is not detached in step S314, the processing proceeds to step S301. When it is determined that the endoscope system 1 is powered off, or the endoscope 100 is detached in step S314, the controller 202 turns off the power of the motor 150 in step S315. Then, the processing returns to the processing of FIG. 2. In this case, the processing of FIG. 2 is terminated.

The method for error display in the present embodiment will be explained. In the present embodiment, error display is performed by using the torque display unit 320. The error display is performed by displaying an error code of a two-digit number, for example. That is, a type of error is associated with an error code in advance, and an error code associated with a particular error is displayed on the torque display unit 320.

Figure 7:
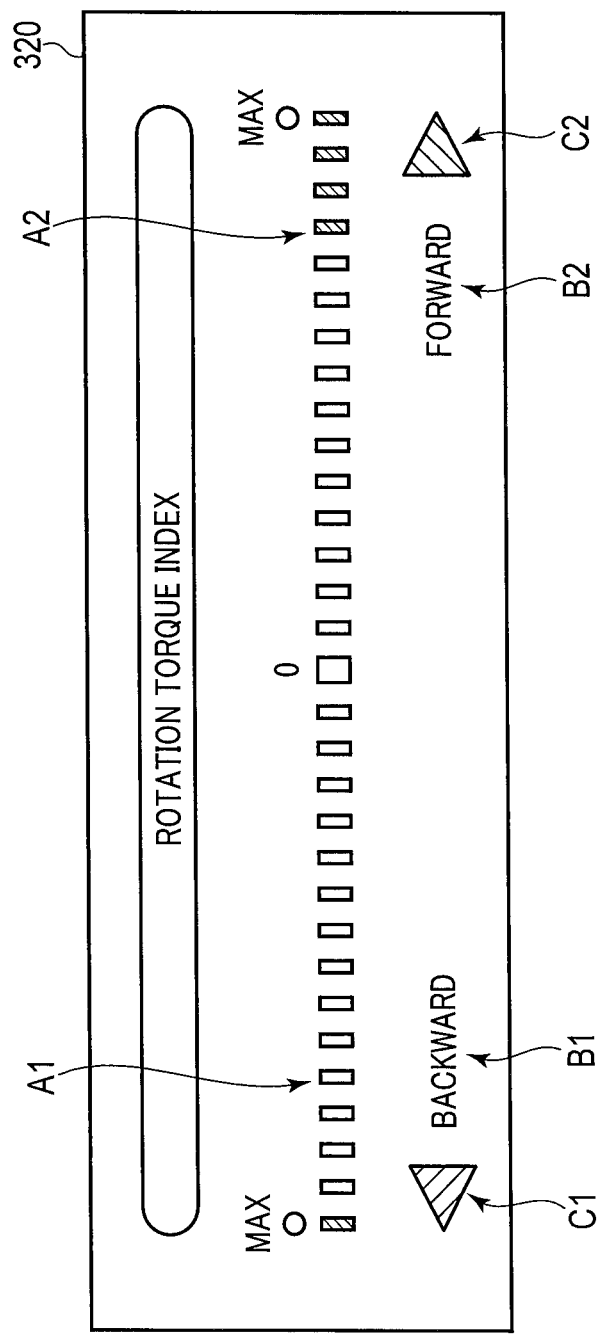
FIG. 7 illustrates an example of error display by the torque display unit.

FIG. 7 illustrates an example of display of an error code by the torque display unit 320. For the error display, the number of levels that are turned on among the nine levels from the left of the removal direction level display part A1 indicates a tens place of an error code. The number of levels that are turned on among the nine levels from the right of the insertion direction level display part A2 indicates a ones place of an error code. For example, when an error code "14" is displayed, the first level from the left of the removal direction level display part A1 is turned on, and four levels from the right of the insertion direction level display part A2 are turned on, as shown in FIG. 7.

As explained above, in the inspection control of the insertion apparatus 1 according to the present embodiment, the removal direction check is performed first, and when the inspection in the removal direction check is normally terminated, the insertion direction check is performed. In addition, during the progress of the removal direction check, the motor 150 is stationary even when the F-pedal 362 is stepped on, in order to allow the movement of the insertion section 110 only in the removal direction. By this operation, the insertion section 110 is prevented from erroneously being inserted in a lumen during the inspection.

Furthermore, in the present embodiment, the inspection control is forcibly terminated when both of the F-pedal 362 and the B-pedal 364 are stepped on at the same time during the inspection control. By this operation, the operation can be transferred to the normal control without performing the inspection control in an emergency.

In addition, the torque display unit of the present embodiment can display any two-digit number. Accordingly, there is no need to provide a display unit for error display independent from the torque display unit 320, thereby reducing the manufacturing costs for the insertion apparatus 1.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An insertion apparatus comprising:
   an insertion section having an elongated shape;
   a rotational housing provided on an outer peripheral surface of the insertion section to be rotatable about a longitudinal axis;
   a motor configured to be controlled to selectively rotate the rotational housing in one of an insertion direction for forward insertion of the insertion section into an internal body and a removal direction for removal of the insertion section from the internal body, along with the rotational housing;

a first foot pedal configured to be manually depressable to rotate the rotational housing in the insertion direction via the motor;

a second foot pedal configured to be manually depressable to rotate the rotational housing in the removal direction via the motor; and a controller configured to switch between an inspection mode and a normal mode, wherein, in the inspection mode, the controller is configured to:

prevent rotation of the motor when the first foot pedal is depressed and the second foot pedal is not depressed thereby preventing rotation of the rotational housing;

prevent rotation of the motor when the first foot pedal and the second foot pedal are depressed thereby preventing rotation of the rotational housing; and rotate the motor when the second foot pedal is depressed and the first foot pedal is not depressed thereby rotating the rotational housing in the removal direction.

2. The insertion apparatus according to claim 1, further comprising:

a motor current detector configured to detect a motor current value of a motor current supplied to the motor, wherein an increasing motor current value corresponds to an increasing speed of rotation, wherein, in the inspection mode, the controller is configured to, after rotating the motor when the second foot pedal is depressed and the first foot pedal is not depressed, stop rotation of the motor when the motor current, detected by the motor current detector, reaches or exceeds a predetermined set value.

3. The insertion apparatus according to claim 2, wherein the controller is configured to terminate control of the motor in the inspection mode when the motor current, detected by the motor current detector, reaches or exceeds the predetermined set value.

4. The insertion apparatus according to claim 2, wherein, in the inspection mode, the controller is configured to control a display to display the motor current value, detected by the motor current detector, and a rotational direction of the motor.

5. The insertion apparatus according to claim 1, wherein, in the normal control mode performed after switching from the inspection mode, the controller is configured to:

rotate the motor when the first foot pedal is depressed and the second foot pedal is not depressed thereby rotating the rotation housing in the insertion direction; and rotate the motor when the second foot pedal is depressed and the first foot pedal is not depressed thereby rotating the rotation housing in the removal direction.

6. The insertion apparatus according to claim 1, wherein the controller is configured to designate a rotational speed of the motor.

7. The insertion apparatus according to claim 1, further comprising a fin formed on an outer peripheral surface of the rotational housing as a spiral shape, and arranged to allow the insertion section to move in the insertion direction into the internal body, or in the removal direction to be removed from the internal body, along with rotation of the rotational housing.

* * * * *